United States Patent [19]

Magni et al.

[11] Patent Number: 4,868,338

[45] Date of Patent: Sep. 19, 1989

[54] METHOD FOR ACYLATING A NAPHTHALENE COMPOUND

[75] Inventors: Ambrogio Magni, Osnago; Giuseppina Visentin, Vedano Al Lambro, both of Italy

[73] Assignee: Blaschim S.p.A., Italy

[21] Appl. No.: 165,704

[22] Filed: Mar. 8, 1988

[30] Foreign Application Priority Data

Mar. 13, 1987 [IT] Italy ................................. 19701 A/87

[51] Int. Cl.$^4$ ............................................. C07C 45/46
[52] U.S. Cl. .................................... 568/319; 568/322; 568/323
[58] Field of Search ......................... 568/319, 322, 323

[56] References Cited

U.S. PATENT DOCUMENTS 4,593,125  6/1986  Davenport et al. ................. 568/319

FOREIGN PATENT DOCUMENTS

| 3530145 | 2/1987 | Fed. Rep. of Germany ...... 568/323 |
| 54-135756 | 10/1979 | Japan ................................... 568/323 |
| 59-51234 | 3/1984 | Japan ................................... 568/323 |
| 60-169435 | 9/1985 | Japan ................................... 568/323 |

OTHER PUBLICATIONS

Chem. Abst., vol. 106, #138,098b (1987).
Chen, Chem. Abst., vol. 106, #213520v (1987).

*Primary Examiner*—James H. Reamer
*Attorney, Agent, or Firm*—Berman, Aisenberg & Platt

[57] ABSTRACT

The acylation of a naphthalene compound, substituted in the 2-position with an electron-donating group, with a reactive derivative of a lower aliphatic acid, in an aprotic organic diluent and in the presence of a Friedel Crafts catalyst consisting of a halide of an element having at least two valences, is improved when maintaining constant at any time the molar ratio of the naphthalene compound to the acylating agent and that of the acylating agent to the Friedel Crafts catalyst within specific ranges.

8 Claims, No Drawings

METHOD FOR ACYLATING A NAPHTHALENE COMPOUND

This invention relates to an improvement in the process for acylating a naphthalene compound, substituted in the 2-position with an electron-donating group, with a reactive derivative of a lower aliphatic acid in an aprotic organic diluent and in the presence of a Friedel Crafts catalyst consisting of a halide of an element having at least two valences.

It is known that the 6-acyl-naphthalenes substituted in the 2-or beta-position with an electron-donating group are useful as precursors of dyestuffs, polyesters, pharmaceuticals and other chemicals.

A typical example is represented by the 6-acyl-2-methoxy-naphthalenes, intermediates useful for preparing naproxen, a well known drug, via several synthetic pathways.

When the acyl group is acetyl, naproxen is preferably prepared via the Darzens reaction. In turn, when the acyl group is propionyl or alpha-halopropionyl, naproxen is preferably prepared by rearranging the corresponding haloketals (European Patent No. 0035305).

The preparation of the 6-acyl-naphthalenes substituted in the 2- or beta-position with an electron-donating group has been, therefore, intensively studied.

Nevertheless, to a great extent this matter is still empirical. Indeed, both the regioselectivity of this reaction and the yield of product acylated in the 6-position can change sharply according to any change in the nature of the electrondonating group, of the acylating agent, of the diluent as well as of the Friedel Crafts catalyst.

As a matter of fact, acylation of a 2-alkyl and 2-alkoxy-naphthalene with an anhydride or a halide of an aliphatic acid in the presence of aluminum chloride proceeds in the 6-position when the diluent is nitrobenzene.

In contrast, acylation of a 2-alkoxy-naphthalene proceeds in the 1-position when the diluent is benzene and carbon sulphide (R.D. Haworth et al., J.C.S. 864, 1934) or a halogenated hydrocarbon (C.A. 60, 476b; U.S. Patents No. 3,758,544 and No. 3,873,594, European Patent No. 0163338 - Example 5).

Acylation of a 2-alkoxy-naphthalene with an aliphatic acid halide in nitrobenzene proceeds in the 6-position even when aluminum chloride is replaced with zinc chloride, ferric chloride or other Friedel Crafts catalysts (U.S. Patent No. 3,803,245).

The reason for these different results has not yet been explained; possibly, they depend on the formation of unknown intermediate complexes (different from case to case) from the components of the reaction mixture (R.B. Girdler et al., J. Chem. Soc. (C), 181, 1966).

It has also been proposed to acylate a 2-alkoxy-naphthalene in a nitroalkane (C.A. 64 12,620 f, 1966) or in a polyphosphoric acid (C.A. 58, 1546 gh. 1963) but these processes have not acquired an industrial significance because the nitroalkanes are very toxic while polyphosphoric acids form very consistent mixtures, require high temperatures, cannot be recycled and are difficult to dispose of.

Notwithstanding many inconveniences, the only process applicable on an industrial scale for acylating regioselectively, in the 6-position, a naphthalene compound substituted in the 2-position with an electron-donating group, remained until some years ago that requiring the use of nitrobenzene and aluminum chloride (Org. Synthesis, 53,5, 1973). Among the main inconveniences of this process, the high cost due to the long working time and to the large amount of energy required are certainly worth mentioning.

The European Patent Application No. 85201466.1 of the Applicant, describes a method that overcomes most of said inconvenience and that comprises acylating a 2-alkoxy-naphthalene with an aliphatic acid and/or a reactive derivative thereof in anhydrous hydrofluoric acid.

This process, however, requires a special airtight sealed plant suitable for continuous working because hydrofluoric acid, which is very corrosive and toxic and which shows a high vapour tension and boils at about room temperature, must be recovered and recycled.

Therefore, the need is still felt for finding the critical conditions wherein acylation of a naphthalene compound, substituted in the 2-position with an electron-donating group, is directed in the 6-position, without requiring a special airtight sealed plant or without being confined to the use of nitrobenzene as a diluent and of aluminum chloride as a catalyst.

Said critical conditions should, anyhow, decrease substantially the costs also when the system nitrobenzene-aluminum chloride is used.

Now, it has been found that all these goals are achieved when maintaining constant at any time the molar ratio of the naphthalene compound to the acylating agent in the range from 1:1 to 1:1.5, and the molar ratio of the acylating agent to the Friedel Crafts catalyst in the range from 1:1 to 1:3.

It is, therefore, an object of this invention to provide a process for acylating a naphthalene compound, substituted in the 2-position with an electron-donating group, with a reactive derivative of a lower aliphatic acid, in an aprotic organic diluent and in the presence of a Friedel Crafts catalyst consisting of a halide of an element having at least two valences, the improvement comprising maintaining constant at any time the molar ratio of the naphthalene compound to the acylating agent in the range from 1:1 to 1:1.5, and the molar ratio of the acylating agent to the Friedel Crafts catalyst in the range from 1:1 to 1:3.

Typical examples of Friedel Crafts catalysts according to this invention are aluminum, zinc and ferric chloride, stannic, antimonic and boron fluoride and the mixtures thereof. Examples of preferred catalysts are aluminum chloride and tin tetrafluoride.

The type of electron-donating group is not a critical feature of this invention, the essential condition being merely that the molar ratio of the naphthalene compound to the acylating agent and the molar ratio of the acylating agent to the Friedel Crafts catalyst are maintained constant at any time within the above mentioned ranges.

Typical examples of electron-donating groups according to this invention are hydroxy, lower alkyl, lower alkoxy, alkylthio and halogen. As used herein, the term "lower" means a group having from 1 to 4 C atoms. Preferred examples of electron-donating groups are hydroxy and methoxy.

The nature of the reactive derivative of the aliphatic acid is not critical either. Typical examples of acylating agents according to this invention are the anhydrides and halides of an acid of the formula $$HOOC-C^*HX-R \qquad (I)$$

in which
R is hydrogen or an alkyl having from 1 to 4 carbon atoms; and
X is hydrogen, halogen or $OSO_2R''$ where, in turn, R'' is methyl, p-methyl phenyl, triphenyl methyl, $CF_3$, or imidazole.

Preferred examples of acylating agents are the acid chlorides and bromides of the formula (I) in which R is hydrogen or methyl and X is hydrogen, bromine or chlorine.

When both X and R are different from hydrogen, the carbon atom marked with an asterisk in the formula (I) is asymmetric.

This invention comprises, therefore, both the use of optically active enantiomers and of their racemic mixtures.

A preferred example of an optically active acylating agent is the 2-chloro propionic acid chloride having (S) configuration.

The nature of the aprotic diluent is not critical either, the only condition being that the diluent does not interact with any component of the reaction mixture so as to hamper the course of the reaction.

Examples of suitable diluents are carbon sulphide as well as the aliphatic and aromatic halogenated hydrocarbons optionally substituted by one or more members of the class comprising halogen, nitro, sulfuric and phosphoric group.

Typical examples of halogenated aliphatic diluents are dichloro methane, chloroform, carbon tetrachloride, 1,2-dichloro ethane and the like. Typical examples of aromatic diluents are nitrobenzene, 1,2- and 1,4-dichloro benzene, 2- and 4-nitro toluene and the like.

The above said diluents can also be used when mixed together.

The constancy of the molar ratios of the naphthalene compound to the acylating agent and of the latter to the Friedel Crafts catalyst in the reaction mixture is obtained by adding to a diluent, at the same time, the predetermined molar quantities of the naphthalene compound, of the acylating agent and of the Friedel Crafts catalyst, optionally dissolved in the same diluent; the Friedel Crafts catalyst is preferably suspended or, more preferably, dissolved in the solution of the acylating agent.

The preferred molar ratio of the naphthalene compound to the acylating agent and the molar ratio of the acylating agent to the Friedel Crafts catalyst are selected within the above mentioned ranges taking into due account their nature and the nature of the selected diluent. However, once the said molar ratios have been determined, they are maintained constant all over the reaction time.

The molar ratio of the acylating agent to the Friedel Crafts catalyst is preferably selected within the range from 1:1 to 1:1.5 when the acylating agent is an acid halide, and within the range from 1:2 to 1:3 when the acylating agent is an acid anhydride.

The temperature is not a critical feature of this invention since the reaction can be carried out at any temperature from $-30°$ C. to the boiling temperature of the reaction mixture, preferably from $-15°$ C. to $120°$ C. The preferred temperature is chosen by taking into due account the usual parameters known to the artisan, such as the exothermic property of the reactants and the reaction speed of the selected system. However, consistently with the selected system, the reaction should preferably be carried out at the highest temperature possible thus reducing the reaction time and increasing the plant productivity.

Substantial and unexpected advantages of the improvement provided by this invention are (i) that the acylation is always directed in the 6-position even when the process is performed in the presence of a diluent which was known to direct in the 1-position and (ii) the significant increase in the productivity. Of course, the latter may be properly appreciated when the process is carried out in the presence of the sole diluent known to direct acylation in the 6-position (i.e. nitrobenzene) even when working according to the old process.

This invention provides, therefore, a very important improvement and overcomes the prejudice well established in the state of the art for many decades, according to which the acylation of a naphthalene compound, substituted in the 2- or beta-position with an electron-donating group, in the presence of a Friedel Crafts catalyst consisting of a halide of an element having at least two valences, proceeds in the 6-position only in nitrobenzene and that, anyhow, the acylation in nitrobenzene involves very long periods of time and, consequently, very high costs.

The artisan will also understand that the economic advantages are even more significant thanks to the great flexibility of the process of this invention that allows a large choice of diluents and/or Friedel Crafts catalysts, case by case.

The following examples illustrate the process of this invention but are not to be construed as limiting.

EXAMPLE 1

A solution of 2-methoxy-naphthalene (22.5 g; 0.14 moles) in 60 ml of nitrobenzene and a solution of $AlCl_3$ (22.7 g; 0.17 moles) and propionyl chloride (16 g; 0.17 moles) in 40 ml of nitrobenzene were added, at the same time, to 20 ml of nitrobenzene, (pre-heated to 75° C.) while maintaining the temperature of the reaction mixture at 70° C.

After 2 hours, the reaction mixture was hydrolized with water (200 ml). The organic phase was separated and washed to neutrality with water; nitrobenzene was evaporated under vacuum.

The residue was crystallized from methanol (50 ml). The crystalline product was collected by filtration and then dried under vacuum.

22.5 g of 6-propionyl-2-methoxy-naphthalene was so obtained, titre, 99% (GLC). Yield, 75%.

EXAMPLE 2

The productivity of the process described in Example 1 above was compared with that of the method described in "Organic Synthesis, 53, 5" except that acetyl chloride was replaced with propionyl chloride.

As used herein, the term "productivity" means the quantity produced per unit of time, the volume of the vessel being the same.

The result obtained are shown in the following

TABLE 1

|  | O.S. | EX. 1 |
| --- | --- | --- |
| Vessel volume | 600 ml | 600 ml |
| 2-methoxy-naphthalene | 75 g | 75 g |
| Propionyl chloride | 56.2 g | 56.2 g |
| Aluminum chloride | 80.9 g | 80.9 g |
| Solvent | 390 ml | 375 ml |
| Reaction time* | 12 h 30' | 2 h |
| 6-propionyl-2-methoxy-naphthalene | 75 g | 75 g |

TABLE 1-continued

| Productivity | 6 g/h | 37.5 g/h |

*The progress of both reactions was monitored by means of GLC analysis and it was established that the time (30' for the addition and 12 hours to complete the reaction) taught by the Organic Synthesis' monography is really the minimum time necessary to obtain at least 95% of acetilated compound because the reaction runs as follows:

| Reaction time | Quantity of 6-propionyl-2-methoxy-naphthalene formed (%) |
|---|---|
| 1 h 20' | 54 |
| 1 h 50' | 60 |
| 2 h 30' | 69 |
| 7 h 15' | 90 |
| 10 h 15' | 93 |
| 12 h 30' | 95 |

EXAMPLE 3

Working in a way similar to that described in Example 1 above but replacing propionyl chloride with acetyl chloride (10.2 g; 0.17 moles), 6-acetyl-2-methoxynaphthalene was obtained; yield, 73%.

In contrast, the method described by "Organic Synthesis, 53, 5" gives a yield of 45%.

EXAMPLE 4

Working in a way similar to that of Example 1 but replacing AlCl$_3$ with SnF$_4$ (33 g; 0.17 moles) and nitrobenzene with methylene chloride, the yield was 78%.

EXAMPLE 5

A solution of AlCl$_3$ (22.7 g; 0.17 moles) and alfa-chloropropionyl chloride (21.6 g; 0.17 moles) in 50 ml of 1,2-dichloroethane and a solution of 2-methoxy naphthalene (22.5 g; 0.14 moles) in 50 ml of 1,2-dichloroethane were added, at the same time, to 20 ml of 1,2-dichloroethane (pre-heated to 70° C.), while maintaining the temperature at 70° C.

After 1.5 hours, the yield in 2-chloro-1-(2'-methoxy-6'-naphthyl)-propan-1-one was 40% (GLC analysis).

EXAMPLE 6

A solution of 2-methoxynaphthalene (22.5 g; 0.14 moles) in 50 ml of methylene chloride and a solution of AlCl$_3$ (19 g; 0.14 moles) and of propionyl chloride (12.9 g; 0.14 moles) in 50 ml of methylene chloride were added, at the same time, to 20 ml of methylene chloride while maintaining the temperature at from 0° to 5° C.

After 2 hours, the reaction mixture contained 3.3 g of 2-methoxynaphthalene and 22.2 g of 6-propionyl-2-methoxy-naphthalene; conversion yield: 85% (GLC analysis).

EXAMPLE 7

A solution of 2-methoxynaphthalene (22.5 g; 0.14 moles) in 50 ml of CH$_2$Cl$_2$ and a solution of AlCl$_3$ (22.7 g; 0.17 moles) and hexanoyl chloride (27.6 g; 0.17 moles) in 50 ml of CH$_2$Cl$_2$ were added at the same time to 20 ml of CH$_2$Cl$_2$ while maintaining the temperature at from 0° to 5° C.

After 1.5 hours, the reaction mixture was hydrolized with water (200 ml), the organic phase was evaporated and washed until neutral with water.

After evaporation and crystallization of the residue from ethanol (200 ml), 25 g of 6-hexanoyl-2-methoxynaphthalene were obtained; yield, 70%.

EXAMPLE 8

A solution of 2-methoxynaphthalene (11.25 g; 0.07 moles) in 50 ml of 1,2-dichlorobenzene and a solution of AlCl$_3$ (11.35 g; 0.085 moles) and of propionyl chloride (8 g; 0.085 moles) in 50 ml of chloroform were added, at the same time, to 10 ml of 1,2-dichlorobenzene, while maintaining the temperature at from 0° to 5° C.

After 30 minutes, the mixture contained 4.5 g of 2-methoxynaphthalene and 21.9 g of 6-propionyl-2-methoxy-naphthalene; conversion yield: 90% (GLC analysis).

EXAMPLE 9

A suspension of ZnCl$_2$ (23.1 g; 0.17 moles) and propionyl chloride (16 g; 0.17 moles) in 80 ml of 1,2-dichlorobenzene and a solution of 2-methoxynaphthalene (22.5 g; 0.14 moles) in 80 ml of 1,2-dichlorobenzene were added at the same time to 20 ml of 1,2-dichlorobenzene, while maintaining the temperature at 75° C.

After 1 hour, the reaction mixture contained 15.9 g of 2-methoxynaphthalene and 5.8 g of 6-propionyl-2-methoxynaphthalene; conversion yield 64.9% (GLC analysis).

EXAMPLE 10

A solution of 2-methoxynaphthalene (11.25 g; 0.07 moles) in 50 ml of methylene chloride and a solution of AlCl$_3$ (24 g; 0.18 moles) and propronic acid anhydride (11.7 g; 0.09 moles) in 50 ml of methylene chloride were added at the same time to 20 ml of methylene chloride, while maintaining the temperature at about 5° C.

After 2 hours, the reaction mixture contained 0.6 g of 2-methoxynaphthalene and 22.2 g of 6-propionyl-2-methoxynaphthalene; conversion yield: 74.7% (GLC analysis).

We claim:

1. In a process for acylating a naphthalene compound, substituted in the 2-position with an electron-donating group, with a reactive derivative of a lower aliphatic acid, as acylating agent, in an aprotic organic diluent and in the presence of a Friedel Crafts catalyst consisting of a halide of an element having at least two valences, the improvement comprising maintaining constant at any time the molar ratio of the naphthalene compound to the acylating agent in the range from 1:1 to 1:1.5, and the molar ratio of the acylating agent to the Friedel Crafts catalyst in the range from 1:1 to 1:3.

2. A process according to claim 1, wherein the electrondonating group in the 2-position of the naphthalene compound is hydroxy, lower alkyl, lower alkoxy, lower alkyltio or halogen.

3. A process according to claim 2, wherein the electrondonating group is methoxy.

4. A process according to claim 1, wherein the acylating agent is a halide or an anhydride of a lower aliphatic acid of formula $$HOOC-C^{*}HX-R \qquad (I)$$

where
R is hydrogen or an alkyl having from 1 to 4 carbon atoms; and
X is hydrogen, halogen or OSO$_2$R" where, in turn, R" is methyl, p-methyl phenyl, triphenyl methyl, CF$_3$ or imidazole.

5. A process according to claim 4, wherein R is hydrogen or methyl and X is hydrogen or chlorine.

6. A process according to claim 1, wherein the Friedel Crafts catalyst is aluminum chloride, tin tetrafluoride or zinc chloride.

7. A process according to claim 1, wherein the aprotic diluent is carbon sulphide or an aliphatic or an aromatic halogenated hydrocarbon optionally substituted by one or more members of the class comprising halogen, nitro, sulfonic and phosphoric group.

8. A process according to claim 1 throughout which the molar ratio of the naphthalene compound to the acylating agent is in the range of from 1:1 to 1:1.5, and the molar ratio of the acylating agent to the Friedel-Crafts catalyst is in the range of from 1:1 to 1:3.

* * * * *